(12) United States Patent
Furukawa et al.

(10) Patent No.: US 8,691,941 B2
(45) Date of Patent: Apr. 8, 2014

(54) METHOD FOR PRODUCING PEPTIDE

(71) Applicant: Ajinomoto Co., Inc., Chuo-ku (JP)

(72) Inventors: Shinya Furukawa, Kawasaki (JP); Hiroki Imai, Kashiwa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/749,978

(22) Filed: Jan. 25, 2013

(65) Prior Publication Data

US 2013/0137853 A1    May 30, 2013

Related U.S. Application Data

(63) Continuation of application No. PCT/JP2011/066714, filed on Jul. 22, 2011.

(30) Foreign Application Priority Data

Jul. 26, 2010  (JP) ................................ 2010-167213

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 1/00* | (2006.01) |

(52) U.S. Cl.
USPC ......................................... 530/314; 530/338

(58) Field of Classification Search
None
See application file for complete search history.

(56) References Cited

U.S. PATENT DOCUMENTS

| | | | |
|---|---|---|---|
| 2006/0149035 A1 | 7/2006 | Rudolph et al. | |
| 2010/0041869 A1 | 2/2010 | Chan et al. | |

FOREIGN PATENT DOCUMENTS

| | | |
|---|---|---|
| JP | 2008-537733 | 9/2008 |
| JP | 2008-301829 | 12/2008 |
| WO | 2012/014808 | 2/2012 |

OTHER PUBLICATIONS

Ternois et al "Ionic Liquids: New Opportunities for the Chemistry of Amino Acids, Peptides, and Pharmaceutical Compounds" Ionic Liquid Applications: Pharmaceuticals, Therapeutics, and Biotechnology. ACS Symposium Series. Published online Apr. 28, 2010.*
Vallette et al "Peptide Synthesis in room temperature ionic liquids" Tetrahedron Letters 45:1617-1619. Published Feb. 16, 2004.*
Noritomi et al "Catalytic activity of alpha-chymotrypsin in enzymatic peptide synthesis in ionic liquids" Biochem Eng J 47:27-30. Published Dec. 1, 2009.*
International Search Report in PCT/JP2011/066714 issued Sep. 13, 2011.
Written Opinion in PCT/JP2011/066714 issued Sep. 13, 2011.
M. Erbeldinger et al., Biotechnol. Prog., vol. 16. No. 6 (2000) p. 1129-1131.
Y. Hu et al., Chinese Journal of Organic Chemistry, vol. 27, No. 10 (2007) p. 1188-1194.
Y. Wu et al., Journal of Bohai University, vol. 29, No. 1 (2008) pp. 1-7.
W. Miao et al., Acc. Chem. Res., vol. 39, No. 12 (2006) pp. 897-908.
W. Miao et al., J. Org. Chem., vol. 70, No. 8 (2005) pp. 3251-3255.
H. Ohno et al., Acc. Chem. Res., vol. 40, No. 11 (2007) pp. 1122-1129.
K. Fukumoto et al., J. Am. Chem. Soc., vol. 127 (2005) pp. 2398-2399.

* cited by examiner

*Primary Examiner* — Cecilia J Tsang
*Assistant Examiner* — Zachary J Miknis
(74) *Attorney, Agent, or Firm* — Oblon, Spivak, McClelland, Maier & Neustadt, L.L.P.

(57) ABSTRACT

Peptides may be produced by using (A) a first amino acid or peptide, which is converted into its ionic liquid form through the formation of an ionic bond, as a substance serving as both a reaction solvent and a reaction starting material; and reacting the first amino acid or peptide with (B) an ester of second amino acid or peptide, in the absence of any peptide hydrolase or any condensation agent, in the presence of water in an amount of not more than 20% by mass relative to the total mass of the reaction system to form a peptide bond between the first amino acid or peptide and the second amino acid or peptide. By means of this process, it is possible to synthesize a peptide at a high concentration and at a high yield, and this method is excellent for producing peptides on an industrial scale.

21 Claims, No Drawings

METHOD FOR PRODUCING PEPTIDE

CROSS REFERENCES TO RELATED APPLICATIONS

This application is a continuation of International Patent Application No. PCT/JP2011/066714, filed on Jul. 22, 2011, and claims priority to Japanese Patent Application No. 2010-167213, filed on Jul. 26, 2010, both of which are incorporated herein by reference in their entireties.

BACKGROUND OF THE INVENTION

1. Field of the Invention

The present invention relates to methods for producing a peptide in a high yield utilizing an ionic liquid. In particular, the present invention relates to methods for producing a peptide on an industrial scale.

2. Discussion of the Background

As it would be anticipated that peptides have a great demand as active components of pharmaceutical products, they have conventionally been produced according to a variety of methods. Then there has recently been proposed a method for producing a peptide utilizing an ionic liquid and such a method has accordingly become of major interest. For instance, JP-T-2008-537733 discloses a method for using an ionic liquid to combine with oligo-peptide, an oligo-saccharide or an oligo-nucleotide for improving the solubility in an organic solvent, and for utilizing as a protective group. However, in this method, a protective group and a condensation agent are required in each polymerization reaction.

In *Biotechnol. Prog.*, 2000, 16: 1129-1131, the reaction: Z-Asp+PM→Z-APM is conducted in an ionic liquid (BP6 [1-butyl-3-methyl-imidazolium hexafluoro phosphate)] utilizing an enzyme (Thermolysin). Thus, it is established that an enzymatic reaction can be carried out even in an ionic liquid. The yield of this reaction is high, on the order of 90%, but the reaction should be conducted at considerably low concentrations of reactants. For this reason, the reaction disclosed in this article is considered to be an enzymatic reaction-in an organic solvent in which a solvent is simply substituted.

In addition, JP-A-2008-301829 discloses the synthesis of a peptide in an ionic liquid (4-methyl-N-butyl-pyridinium tetrafluoro borate). The synthesis herein is also considered to be an enzymatic reaction-in an organic solvent in which a solvent is simply substituted, as in *Biotechnol. Prog.*, 2000, 16: 1129-1131. Moreover, in this synthesis, the reaction is carried out at a considerably low concentration, on the order of 20 mM, and the reaction requires the use of a protective group.

*Acc. Chem. Res.*, 2007, 40: 1122-1129 establishes that an amino acid can be converted into its ionic liquid form by combining the amino acid with a residual group of an ionic liquid through an ionic bond. Although the document does not discuss its application, a use for an electrolyte of a fuel cell has initially been investigated.

"Advance in Liquid-Phase Organic Synthesis Using Functional Ionic Liquid as Supports", Nanjing University of Technology, HU Yi, LI Heng, HUANG He, WEI Ping, Issued on March, 2007, describes a review of the synthesis of polypeptides, oligosaccharides or other organic substances using an ionic liquid and the gist thereof describes that a substrate-ionic liquid is used as an intermediate for such a synthesis. However, there is no specific data.

"Progress on Amino Acid-Ionic Liquid", Liaoning University, WU Yang, ZHANG Tian-tian, SONG Xi-ming, Issued on March, 2008, discloses an introductory review of an ionic liquid combined with an amino acid. it refers to the applications thereof as a solvent or a catalyst in the near future, although there is not disclosed therein any specific data at all.

However, the methods for synthesizing a peptide utilizing an ionic liquid, which have been proposed until now, provide the peptide in a low yield and neither of them is a method for producing a peptide in an industrial scale.

Thus, there remains a need for improved processes for producing a peptide in a high yield utilizing an ionic liquid.

SUMMARY OF THE INVENTION

Accordingly, it is one object of the present invention to provide novel for producing a peptide in a high yield utilizing an ionic liquid.

It is another object of the present invention to provide novel methods for producing a peptide at a high concentration and in a high yield utilizing an ionic liquid and, in particular, to a method for producing a peptide on an industrial scale.

These and other objects, which will become apparent during the following detailed description, have been achieved by the inventors' discovery that using a first amino acid or peptide, which is converted into its ionic liquid form through the formation of an ionic bond, as a reaction solvent and a reaction starting material; and reacting the first amino acid or peptide, which is converted into its ionic liquid form, with an ester of second amino acid or peptide in the presence of water in an amount of not less than a predetermined level, leads to obtaining a peptide at a high concentration and in a high yield without using any peptide hydrolase.

More specifically, the present invention herein provides a method for producing a peptide, which comprises the steps of using (A) a first amino acid or peptide, which is converted into its ionic liquid form through the formation of an ionic bond, as a substance serving as both a reaction solvent and a reaction starting material; and reacting the first amino acid or peptide, which is converted into its ionic liquid form, with (B) an ester of second amino acid or peptide, in the absence of any peptide hydrolase or any condensation agent and in the presence of water in an amount of not more than 20% by mass (preferably not more than 10% by mass) relative to the total mass of the reaction system to form a peptide bond between the first amino acid or peptide and the second amino acid or peptide.

According to the present invention, a peptide can be synthesized at a high concentration and in a high yield without using any peptide hydrolase. Thus, the present invention has such a substantial merit to the effect that any step for decomposing a peptide hydrolase can be omitted, from the industrial standpoint.

DETAILED DESCRIPTION OF THE PREFERRED EMBODIMENTS

First of all, (A) a first amino acid or peptide, which is converted into its ionic liquid form through the formation of an ionic bond, is used as a reaction solvent and a reaction starting material, in the present invention. In this respect, the first amino acid or peptide is converted into its ionic liquid form through the formation of an ionic bond of corresponding amino acid or peptide and a cation derived from a quaternary hetero atom-containing compound such as one selected from the group consisting of a quaternary phosphonium salt, a quaternary ammonium salt, an imidazolium salt, a pyridinium salt, a pyrrolidinium salt and a piperidinium salt. More specifically, a first amino acid or peptide is converted into its ionic liquid form through an ionic bond of the corresponding amino acid or peptide and at least one cation selected from the group consisting of alkyl phosphonium ions, alkyl imidazolium ions, alkyl ammonium ions, alkyl pyridinium ions, alkyl pyrrolidinium ions and alkyl piperidinium ions. The number of carbon atoms of each of the alkyl groups included in the foregoing alkyl phosphonium ions or the like, preferably falls within the range of from 1 to 12, more preferably 1 to 6 and most preferably 1 to 4. In the instance where such a quaternary cation contains a plurality of alkyl groups, the alkyl groups may be the same or different from one another, but they are preferably identical to one another. More specifically, preferred examples of the foregoing quaternary cations include a tetrabutyl phosphonium ion, a tetraethyl phosphonium ion, a tetramethyl quaternary ammonium ion, a tetraethyl quaternary ammonium ion, a tetrabutyl quaternary ammonium ion, a hexyl triethyl quaternary ammonium ion, a 1-ethyl-3-methyl-imidazolium ion, a 1,3-dimethyl-imidazolium ion, a 1-butyl-3-methyl-imidazolium ion, a 1-butyl-3-methyl-pyridinium ion, a 1-butyl-pyridinium ion and a 1-methyl-1-butyl-pyrrolidinium ion. These quaternary cations can easily be available in the form of, for instance, hydrochlorides, hydrobromides and hydroxides thereof from, for instance, Tokyo Chemical Industries, Co., Ltd., Hokko Chemical Co., Ltd., and Toyo Synthetic Chemical Co., Ltd.

In this connection, the term "ionic liquid" in this specification does not mean any molten or fused salt, but means a salt constituted by an ion, which can be fused at a low temperature of not higher than 100° C. Accordingly, water never falls within the purview of the ionic liquid to be used herein.

In the present invention, the foregoing first amino acid or peptide may be, for instance, an essential amino acid such as proline (Pro), tyrosine (Tyr), phenylalanine (Phe), leucine (Leu), glycine (Gly), methionine (Met), serine (Ser), alanine (Ala), aspartic acid (Asp), glutamine (Gln), glutamic acid (Glu), histidine (His), lysine (Lys), and valine (Val) and analogues of these amino acids as well as oligomers and polymerized products (polymers) thereof. Among these substances, amino acids having an aromatic ring or a hetero ring within the molecule and oligomers containing the same as their constituents are preferably used, particularly, those having a secondary amino group within the molecule are preferred.

The amino group present in each of these amino acids or peptides may be protected with an amino-protecting group such as a formyl group, a benzyloxy-carbonyl group or a butoxycarbonyl group. However in the present invention, it is preferred to use amino acids or peptides which are not protected at all.

In the present invention, the foregoing quaternary hetero atom-containing compound and the first amino acid or peptide can be mixed together in approximately equivalent molar amounts; and the water in the resulting mixture can then be evaporated by heating the mixture (preferably at a temperature ranging from 40 to 70° C.) under ordinary pressure or under reduced pressure (preferably at a pressure ranging from about 2.7 kPa to about 20 kPa (20 to 150 mmHg)) to subject the mixture to a dehydration condensation reaction and to thereby form the corresponding first amino acid or peptide, which is converted into its ionic liquid form.

In the present invention, preferably used as (A) the first amino acid or peptide, which is converted into its ionic liquid form is a carboxylate, i.e., the first amino acid or peptide is ionically bonded to the foregoing quaternary hetero atom-containing compound through the carboxyl group present in the first amino acid or peptide.

In this respect, the disclosure of Acc. Chem. Res., 2007, 40: 1122-1129, which relates to quaternary hetero atom-containing compounds, amino acids and peptides as well as amino acids or peptides converted into their ionic liquid forms) is incorporated herein by reference in its entirety.

In the present invention, the second component, which is to be reacted with (A) the foregoing component, are (B) esters of second amino acid or peptide. The esters of amino acid or peptide used herein may be a ester of, for instance, essential amino acids such as proline (Pro), tyrosine (Tyr), phenylalanine (Phe), leucine (Leu), glycine (Gly), methionine (Met), serine (Ser), alanine (Ala), aspartic acid (Asp), glutamine (Gln), glutamic acid (Glu), histidine (His), lysine (Lys), and valine (Val) and analogues of these amino acids as well as oligomers and polymerized products (polymers) thereof, whose carboxyl group has been esterified with, for instance, alkyl groups.

The alkyl groups may preferably have 1 to 12 carbon atoms, more preferably 1 to 6 carbon atoms and particularly preferably 1 to 4 carbon atoms. These esters may be used alone or in any combination of at least two of them. In addition, a component (B) may be in a form of an acid-addition salt derived from an inorganic acid, for instance, hydrochloride.

Among the foregoing components, alanine (Ala) methyl ester, glycine (Gly) methyl ester and arginine (Arg) methyl ester are preferable, and particularly acid-addition salts thereof derived from inorganic acids, for instance, hydrochlorides, are preferable.

In the present invention, it is preferred that the second amino acid or peptide is not protected at its amino group, but the second amino acids or peptides may be protected at its amino group.

The present invention is characterized in that (A) the aforementioned first amino acid or peptide, which is converted into its ionic liquid form through the formation of an ionic bond, is used as a reaction solvent and a reaction starting material, and that the component (A) is then reacted with (B) the foregoing ester of second amino acid or peptide. More specifically, there is substantially no reaction solvent other than the component (A), i.e. the first amino acid or peptide, which is converted into its ionic liquid form. In other words, the reaction proceeds in such a condition that the component (B), i.e. the ester of second amino acid or peptide, is dissolved in the component (A). For this reason, the component (A) is used in an amount of not less than an equimolar amount relative to the component (B), preferably at a molar ratio, i.e. the molar amount of the first amino acid: that of the second amino acid, ranging from 20:1 to 1:1, and more preferably 10:1 to 2:1. However, in the instance where the component (B) has a poor solubility in the component (A), undissolved state of (B) the ester of second amino acid or peptide would gradually be dissolved in the component (A) along with the progress of the reaction of the component (A) with the component (B). Therefore the ratio between the amounts of the components (A) and (B) may be determined depending on the characteristic properties of these components (A) and (B).

According to the present invention, the first amino acid or peptide, which is converted into its ionic liquid form, may be used as a reaction solvent and a reaction starting material and may be reacted with the esters of second amino acid or peptide in such a condition that the first amino acid or peptide is present in excess. This accordingly permits the selective production of an intended peptide without introducing any protective group into the second amino acid or peptide. Moreover, the present invention also has such a merit that the reaction proceeds without adding any additive or catalyst to the reaction system for promoting the formation of an intended peptide, such as an enzyme or peptide-condensation agent.

In the present invention, it would be preferred to form a peptide bond between the amino group present on the first amino acid or peptide and the carboxyl group on the second amino acid or peptide according to the foregoing reaction. In this reaction, the ester bond of the ester of second amino acid or peptide is opened or cleaved and thus an alcohol is also formed from the alcoholic oxygen atom (or alcoholic group) which constitutes the ester.

The present invention is further characterized in that in some embodiments the component (A) is reacted with the component (B) in the absence of any peptide hydrolase or any condensation agent and in the presence of water in an amount of not more than 20% by mass (preferably not more than 10% by mass) relative to the total mass of the reaction system to form a peptide bond between the first amino acid or peptide and the second amino acid or peptide. The present invention does not use a peptide hydrolase at all, while the conventional techniques require to use the peptide hydrolase. Accordingly, the present invention has such industrial advantages that the production cost required for the formation of an intended peptide and that the present invention permits the elimination of any step required for the removal of the used peptide hydrolase.

In some embodiments, the reaction system in which the peptide bond is formed is substantially free of any peptide hydrolase and/or coupling agent. By substantially free of peptide hydrolase, it is meant that the reaction system contains less than 1% by mass of a peptide hydrolase, preferably less than 0.1% by mass of a peptide hydrolase, more preferably less than 0.01% by mass of a peptide hydrolase, based on the total weight of the reaction system. By substantially free of coupling agent, it is meant that the reaction system contains less than 1 molar equivalent of a coupling agent, preferably less than 0.1 molar equivalent of a coupling agent, more preferably less than 0.01 molar equivalent of a coupling agent, with respect to the component (A).

In the present invention, it is preferred that (A) the first amino acid or peptide, which is converted into its ionic liquid form, is reacted with (B) the ester of second amino acid or peptide, under a condition that the water present in the reaction system is dissolved or dispersed in (A) the first amino acid or peptide, which is converted into its ionic liquid form, and at least part of (B) the ester of second amino acid or peptide is dissolved in (A) the first amino acid or peptide, which is converted into its ionic liquid form.

It is necessary to adjust the amount of water present in the reaction system to a level of not more than 20% by mass, preferably not more than 10% by mass and more preferably 0 to 5% by mass, on the basis of the total mass of the reaction system, and the reaction is preferably conducted under such a condition that the reaction system is substantially free of any water.

In the present invention, the reaction system contains only a small amount of water and it is preferably substantially or completely free of water and therefore, the reaction can be conducted without adjusting the pH value of the reaction system.

The peptide hydrolase herein is likely at least one member selected from the group consisting of proteases, peptidases and hydrolases and most likely is Thermolysin. Such an enzyme can easily be available from Sigma-Aldrich Corporation.

Generally and widely used as condensation agents in the chemical synthesis are N,N'-carbonyl-diimidazole, N,N'-dicyclohexyl-carbodiimide and 1-ethyl-3-(3-dimethylaminopropyl)-carbodiimide hydrochloride, and such condensation agents can easily be available from, for instance, Kanto Chemical Co., Ltd. and WAKO Pure Chemical Co., Ltd.

In the present invention, the reaction of (A) the first amino acid or peptide, which is converted into its ionic liquid form, with (B) the ester of second amino acid or peptide is preferably carried out by mixing these two components together, while maintaining the mixture at a temperature ranging from 0 to 100° C., preferably room temperature (20° C.) to 70° C. The completion of the reaction is preferably confirmed by detecting the end point of the peptide-forming reaction according to the HPLC technique, the final reaction product is preferably isolated by means of, for instance, a method utilizing a resin, a method utilizing an organic solvent, and a method utilizing the crystallization technique, and the identification of the reaction product is desirably carried out according to the HPLC technique.

The HPLC technique may be carried out according to the usual procedures, but is preferably carried out under the following conditions:

Preferably used as the column for the HPLC analysis is GL Sciences Inertsil ODS-3:4.6 mm I.D.×250 mm. The HPLC procedures are carried out under the following conditions: 40° C.; a flow rate of 1.5 mL/min; a mobile phase A used comprising 100 mM of $KH_2PO_4$ and 5 mM of sodium 1-octanesulfonate; a mobile phase B used comprising 100% acetonitrile, wherein these mobile phases are passed through the column according to the isocratic elution technique, at a mixing ratio: A/B of 200:1; a pH value of 2.2; a detection wavelength of 210 nm; a stop time of 39 mM; and an injection volume of 10.0 µL (Condition 1). Alternatively, it is preferred that, in the condition 1, a mixing ratio: A/B of 90:10 is substituted for the mixing ratio: A/B of 200:1 (Condition 2). Moreover, the HPLC procedures can likewise be carried out under the following conditions: 40° C.; a flow rate of 1.5 mL/min; a mobile phase A used comprising 50 mM of $NaH_2PO_4$ and 5 mM of sodium 1-octanesulfonate; a mobile phase B used comprising 100% MetOH, wherein these mobile phases are passed through the column according to the isocratic elution technique, at a mixing ratio: A/B of 5:1; a pH value of 2.1; a detection wavelength used: 210 nm; a stop time of 39 min; and an injection volume of 10.0 µL (Condition 3).

In the instance where the first and second amino acids or peptides, whose amino groups or carboxyl groups are protected, are used as the reaction starting materials, these protective groups may be eliminated or removed (deblocking) according to the usual technique such as a catalytic reduction technique.

The peptides (oligopeptides or polypeptides) prepared by the synthetic method according to the present invention can widely be used as effective components for foods including, for instance, functional foods and seasonings, nutrient compositions such as infusions and livestock feeds; active components for pharmaceutical products; or effective components for a variety of chemical reagents.

Other features of the invention will become apparent in the course of the following descriptions of exemplary embodiments which are given for illustration of the invention and are not intended to be limiting thereof.

EXAMPLES

Example 1

Effect on Dipeptide-Forming Reaction of Using Amino Acid; Proline (L-Pro), which is Converted into its Ionic Liquid Form, Serving as Reaction Starting Material and as Reaction Solvent to Increase the Concentration of the Amino Acid Equimolar amounts of commercially available L-proline (L-Pro) and a 40% by mass solution of tetrabutyl phosphonium hydroxide (hereunder referred to as "TBP-OH") (mixing ratio: L-Pro/TBO-OH=1:1) were blended together (50 g in total), the resulting mixture was then stirred in a water bath warmed at 60° C., the pressure of the reaction system was about 6.7 kPa (50 mmHg) to make the water evaporate from the reaction system and to thereby allow a dehydration condensation reaction to take place (water content: 2% by mass). The obtained L-proline-tetrabutyl phosphonium (hereunder referred to as "L-Pro-TBP") was found to be a colorless and transparent liquid.

L-alanine methyl ester hydrochloride (hereunder referred to as "L-Ala-OMe.HCl") was dissolved in the foregoing L-Pro-TBP obtained according to the foregoing procedures, in such a manner that the concentration of the L-Ala-OMe-.HCl was controlled to a level of 1.000 mmol per unit mass (1 kg) of the L-Pro-TBP (1.000 mmol/kg-L-Pro-TBP; the amount of water relative to the total mass of the reaction system: 2% by mass). After the addition of L-Ala-OMe.HCl, the mixture was stirred enough to ensure the mixture uniform, and then, the reaction of these components was initiated by stirring the same in a water bath while heating it to a temperature of 37° C. The reaction was finished 72 hours after the initiation of the reaction, and samples, which were collected at appropriate intervals of time during the reaction, were analyzed according to the HPLC technique to confirm the formation of the intended dipeptide, i.e., L-alanyl proline (L-Ala-Pro).

The amino acid, i.e. L-Pro and L-Ala-OMe.HCl used here were commercially available, and they were purchased from Sigma Company. In addition, TBP-OH was purchased from Hokko Chemical Industry Co., Ltd.

The yield of L-Ala-Pro obtained 72 hours after the initiation of the foregoing reaction was found to be 31.0% by mole relative to the amount of L-Ala-OMe.HCl added to the reaction system at the initiation of the reaction.

Example 2

Effect of Reaction Temperature on L-Ala-Pro-Forming Reaction

L-Ala-OMe.HCl was added to the L-Pro-TBP prepared by the conversion of L-Pro into its ionic liquid form according to the method disclosed in Example 1 so as to control the concentration of the L-Ala-OMe.HCl to 1.000 mmol per unit mass (1 kg) of the L-Pro-TBP (the amount of water relative to the total mass of the reaction system: 2% by mass). The mixture was stirred enough to ensure the mixture uniform, and then, the reaction of these components was initiated while stirring the reaction system in a water bath and warming the same at 37° C. or 50° C. The reaction was finished 72 hours after the initiation of the reaction, and the samples, which were collected at appropriate intervals of time during the reaction, were analyzed according to the HPLC technique to confirm the formation of the desired dipeptide, i.e., L-Ala-Pro. The results are summarized in the following Table 1.

TABLE 1

| | Reaction Temperature (° C.) | |
|---|---|---|
| | 37 | 50 |
| Yield of L-Ala-Pro (%) | 31.0 | 32.0 |

Example 3

Effect of Concentration of L-Ala-OMe.HCl on L-Ala-Pro-Forming Reaction

L-Ala-OMe was added to the L-Pro-TBP prepared by the conversion of L-Pro into its ionic liquid form according to the method disclosed in Example 1 so as to control the concentrations of the L-Ala-OMe to 500 mmol/kg-Pro-TBP and 1.000 mmol/kg-Pro-TBP, respectively (the amount of water relative to the total mass of the reaction system: 2% by mass). Thereafter, the reaction of these components was initiated by heating the reaction system to 50° C., while stirring the same in a water bath. The reaction was finished 72 hours after the initiation of the reaction, and samples, which were collected at appropriate intervals of time during the reaction, were analyzed according to the HPLC technique to confirm the formation of the desired dipeptide, i.e., L-Ala-Pro. The results are summarized in the following Table 2.

TABLE 2

| | Concentration of Ala-OMe | |
|---|---|---|
| | 500 mmol/ kg-Pro-TBP | 1,000 mmol/ kg-Pro-TBP |
| Yield of L-Ala-Pro (%) | 36.4 | 32.0 |

Example 4

Effect on Dipeptide-Forming Reaction of Using Amino Acid; Tyrosine (L-Tyr), which is Converted into its Ionic Liquid Form, Serving as Reaction Starting Material And as Reaction Solvent to Increase the Concentration of the Amino Acid Commercially available L-tyrosine (L-Tyr) and TBP-OH were blended at a mixing ratio: L-Tyr/TBP-OH of 1:1.2 (molar ratio), then the resulting mixture was stirred in a water bath warmed at 60° C., while reducing the pressure to a level of about 6.7 kPa (50 mmHg) to thereby subject the mixture to a dehydration condensation reaction, while the water generated during the reaction was evaporated. The L-tyrosine-tetrabutyl phosphonium (hereunder referred to as "L-Tyr-TBP") obtained was found to be a colorless and transparent liquid (in this respect, the water content of the product was found to be 2% by mass).

To the L-Tyr-TBP prepared above by converting amino acid tyrosine into its ionic liquid form, glycine methyl ester hydrochloride (hereunder referred to as "Gly-OMe.HCl") was added in such a manner that the concentration thereof was set at a level of 1.000 mmol/kg-L-Tyr-TBP. After the addition of the Gly-OMe.HCl, the mixture was stirred enough to ensure the mixture uniform, and then, the reaction of the mixture was initiated by heating the same at 37° C., while stirring the reaction system in a water bath (the amount of water relative to the total mass of the reaction system: 2% by mass). The reaction was finished 48 hours after the initiation of the reaction, and samples, which were collected at appropriate intervals of time during the reaction, were analyzed according to the HPLC technique to confirm the formation of the intended dipeptide, i.e., glycyl tyrosine (Gly-Tyr).

The amino acids L-Tyr and Gly-OMe.HCl used in the foregoing reaction are commercially available, and they were purchased from Sigma Company.

The yield of the Gly-Tyr obtained 48 hours after the initiation of the foregoing reaction was found to be 3.9% by mole relative to the amount of Gly-OMe.HCl added to the reaction system at the initiation of the reaction.

Example 5

Effect of Reaction Temperature on Gly-Tyr-Forming Reaction

Gly-OMe.HCl was added to the L-Tyr-TBP prepared by converting L-Tyr into its ionic liquid form according to the method described in Example 4 such that the concentration of the former was set at a level of 1.000 mmol/kg-L-Tyr-TBP (the amount of water present in the reaction system relative to the total mass of the system: 2% by mass). Then, the mixture was stirred enough to ensure the mixture uniform. Thereafter, the mixture was heated to 37° C. or 60° C., while stirring the same in a water bath. The reaction was finished 48 hours after the initiation of the reaction, and samples, which were collected at appropriate intervals of time during the reaction, were analyzed according to the HPLC technique to confirm the formation of the intended dipeptide, i.e., L-Gly-Tyr. The results are listed in the following Table 3.

TABLE 3

|  | Reaction Temperature (° C.) | |
| --- | --- | --- |
|  | 37 | 60 |
| Yield of L-Gly-Tyr (%) | 3.9 | 4.1 |

As is clear from the results above Tables 1 and 3, there was not observed any difference in the yield of L-Gly-Tyr while the reaction temperature was set at a level ranging from 30 to 70° C.

Example 6

Effect of Concentration of Gly-OMe.HCl on Gly-Tyr-Forming Reaction

Gly-OMe.HCl was added to the L-Tyr-TBP prepared by converting L-Tyr into its ionic liquid form according to the method described in Example 4 such that the concentration of the former was set at a level of 500 mmol/kg-L-Tyr-TBP or 1.000 mmol/kg-L-Tyr-TBP (the amount of water present in the reaction system relative to the total mass of the system: 2% by mass). Then, the mixture was stirred enough to ensure the mixture uniform. Thereafter, the mixture was heated to 37° C. or 60° C., while stirring the same in a water bath. The reaction was finished 48 hours after the initiation of the reaction, and samples, which were collected at appropriate intervals of time during the reaction, were analyzed according to the HPLC technique to confirm the formation of the intended dipeptide, i.e., L-Gly-Tyr. The results at 37° C. and at 60° C. are summarized in the following Tables 4 and 5, respectively.

TABLE 4

|  | Concentration of L-Gly-OMe•HCl | |
| --- | --- | --- |
|  | 500 mmol/ kg-L-Tyr-TBP | 1000 mmol/ kg-L-Tyr-TBP |
| Yield of L-Gly-Tyr (%) | 4.9 | 3.9 |

TABLE 5

|  | Concentration of L-Gly-OMe•HCl | |
| --- | --- | --- |
|  | 500 mmol/ kg-L-Tyr-TBP | 1000 mmol/ kg-L-Tyr-TBP |
| Yield of L-Gly-Tyr (%) | 5.6 | 4.1 |

The results shown in Tables 2, 4, and 5 clearly indicate that the molar ratio between the first amino acid and the second amino acid preferably falls within the range of from 2:1 to 1:1.

Example 7

Synthesis of Dipeptide, i.e., Gly-Gly

Equimolar amounts of commercially available glycine (Gly) and a 40% by mass solution of TBP-OH (Gly/TBP-OH=1:1) (the amount of these components was 50 g in total) were blended, the resulting mixture was then stirred in a water bath warmed at 60° C., while the pressure of the reaction system was reduced to about 6.7 kPa (50 mmHg) to make the water evaporate from the reaction system and to thereby allow a dehydration condensation reaction of these components to take place (the water content: 16% by mass). The glycine-tetrabutyl phosphonium (hereunder referred to as "Gly-TBP") obtained was found to be a colorless and transparent liquid.

Glycine methyl ester hydrochloride (hereunder referred to as "Gly-OMe.HCl") was dissolved in the foregoing Gly-TBP obtained by converting Gly into its ionic liquid form according to the foregoing procedures so as to adjust the concentration of the Gly-OMe.HCl to 1.000 mmol/kg-Gly-TBP (the amount of water relative to the total mass of the reaction system: 16% by mass). After the addition of Gly-OMe.HCl, the mixture was stirred enough to ensure the mixture uniform, and then, the reaction of these components was initiated by stirring the same in a water bath while heating the reaction system to 60° C. The reaction was finished 3 hours after the initiation of the reaction, and samples, which were collected at appropriate intervals of time during the reaction, were analyzed according to the HPLC technique to confirm the formation of the intended dipeptide, i.e., glycyl glycine (Gly-Gly).

Alternatively, the same procedures used above were repeated except that the reaction was carried out at 37° C. for 17 hours instead of carrying out the reaction at 60° C. for 3 hours to prepare a dipeptide, i.e., Gly-Gly and to confirm the formation of the same.

The amino acid, i.e. Gly and Gly-OMe.HCl used above are commercially available, and they were purchased from Sigma Company. In addition, TBP-OH likewise used above was purchased from Hokko Chemical Industry Co., Ltd.

The yield of the dipeptide, i.e., Gly-Gly obtained by the foregoing reaction carried out at 60° C. for 3 hours was found to be 73.0% by mole relative to the amount of Gly-OMe.HCl added to the reaction system at the initiation of the reaction.

In addition, the yield of the dipeptide, i.e., Gly-Gly obtained by the foregoing reaction carried out at 37° C. for 17 hours was found to be 58.0% by mole relative to the amount of Gly-OMe.HCl added to the reaction system at the initiation of the reaction.

Example 8

Synthesis of Dipeptide, i.e. L-Ala-Gln

Equimolar amounts of commercially available L-glutamine (L-Gln) and a 40% by mass solution of TBP-OH (L-Gln/TBP-OH=1:1) (50 g in total) were blended, the resulting mixture was then stirred in a water bath warmed at 60° C., while the pressure of the reaction system was reduced to about 6.7 kPa (50 mmHg) to make the water evaporate from the reaction system and to thereby allow a dehydration condensation reaction of these components to take place (the water content of the reaction system: 7% by mass). The L-glutamine-tetrabutyl phosphonium (hereunder referred to as "L-Gln-TBP") obtained was found to be a colorless and transparent liquid.

L-alanine methyl ester hydrochloride (hereunder referred to as "L-Ala-OMe.HCl") was dissolved in the foregoing L-Gln-TBP obtained by converting L-Gln into its ionic liquid form according to the foregoing procedures such that the concentration of the L-Ala-OMe.HCl was controlled to 200 mmol/kg-L-Gln-TBP (the amount of water relative to the total mass of the reaction system: 7% by mass). After the addition of L-Ala-OMe.HCl, the mixture was stirred enough to ensure the mixture uniform, and then, the reaction of these components was initiated by stirring the same in a water bath while heating the reaction system to 60° C. The reaction was finished 23 hours after the initiation of the reaction, and samples, which were collected at appropriate intervals of time during the reaction, were analyzed according to the HPLC technique to confirm the formation of the intended dipeptide, i.e., L-alanyl glutamine (L-Ala-Gln).

Alternatively, the same procedures used above were repeated except that the reaction was carried out at 37° C. for 3 hours instead of carrying out the reaction at 60° C. for 23 hours to prepare the desired dipeptide, i.e., L-Ala-Gln and to confirm the formation of the same.

The amino acids, i.e., L-Gln and L-Ala-OMe.HCl used above are commercially available, and they were purchased from Sigma Company and Tokyo Chemical Industry Co., Ltd., respectively. In addition, TBP-OH likewise used above was purchased from Hokko Chemical Industry Co., Ltd.

The yield of the dipeptide, i.e., L-Ala-Gln obtained by the reaction carried out at 60° C. for 23 hours was found to be 2.0% by mole relative to the amount of L-Ala-OMe.HCl added to the reaction system at the initiation of the reaction.

In addition, the yield of L-Ala-Gln obtained by the reaction carried out at 37° C. for 3 hours was found to be 3.8% by mole relative to the amount of L-Ala-OMe.HCl added to the reaction system at the initiation of the reaction.

Example 9

Synthesis of Dipeptide, i.e., L-Arg-Gln

Commercially available L-glutamine (L-Gln) and a 40% by mass solution of TBP-OH in a mixing ratio: L-Gln/TBP-OH of 1:1.2 (50 g in total) were blended, the resulting mixture was then stirred in a water bath warmed at 60° C., while the pressure of the reaction system was reduced to about 6.7 kPa (50 mmHg) to make the water evaporate from the reaction system and to thereby allow a dehydration condensation reaction of these components to take place (the water content of the reaction system: 14% by mass). The L-glutamine-tetrabutyl phosphonium (hereunder referred to as "L-Gln-TBP") obtained was found to be a colorless and transparent liquid.

L-arginine methyl ester hydrochloride (hereunder referred to as "L-Arg-OMe.HCl") was dissolved in the foregoing L-Gln-TBP prepared above by converting L-Gln into its ionic liquid form according to the foregoing procedures such that the concentration of the L-Arg-OMe.HCl was adjusted to 800 mmol/kg-L-Gln-TBP (the amount of water relative to the total mass of the reaction system: 14% by mass). After the addition of L-Arg-OMe.HCl, the mixture was stirred enough to ensure the mixture uniform, and then, the reaction of these components was initiated by stirring the same in a water bath while heating the reaction system to 60° C. The reaction was finished 20 hours after the initiation of the reaction, and samples, which were collected at appropriate intervals of time during the reaction, were analyzed according to the HPLC technique to confirm the dipeptide, i.e., L-Arg-Gln.

The amino acid, i.e., L-Gln and L-Arg-OMe.HCl used above are commercially available, and they were purchased from Sigma Company and BACHEM Company, respectively. In addition, TBP-OH likewise used above was purchased from Hokko Chemical Industry Co., Ltd.

The yield of L-Arg-Gln obtained by the reaction carried out at 60° C. for 20 hours was found to be 1.0% by mole relative to the amount of L-Arg-OMe.HCl added to the reaction system at the initiation of the reaction.

Example 10

Synthesis of Dipeptide, i.e., Gly-Gln

The same procedures used in Example 9 were repeated except that glycine methyl ester hydrochloride (hereunder referred to as Gly-OMe.HCl) was dissolved in L-Gln-TBP prepared by converting L-glutamine (L-Gln) into its ionic liquid form according to the same method used in Example 9 such that the concentration of the former was adjusted to 900 mmol/kg-L-Gln-TBP (the amount of water relative to the total mass of the reaction system: 14% by mass) and that the reaction time was changed from 20 hours to 23 hours to form the intended dipeptide, i.e., glycyl glutamine (Gly-Gln) and in this respect, the formation of such a desired dipeptide was confirmed according to the HPLC technique.

The amino acids L-Gln and Gly-OMe.HCl used above are commercially available, and they were purchased from Sigma Company and WATANABE Chemical Industry Co., Ltd., respectively.

The yield of the dipeptide, i.e., Gly-Gln obtained by the reaction carried out at 60° C. for 23 hours was found to be 2.0% by mole relative to the amount of L-Gly-OMe.HCl added to the reaction system at the initiation of the reaction.

Example 11

Synthesis of Dipeptide, i.e., Arg-Ala

The same procedures used in Example 9 were repeated except that L-Ala-TBP, which was purchased from KATAYAMA Drug-Manufacturing Laboratory was used in place of the L-Gln-TBP employed in Example 9, that L-arginine methyl ester hydrochloride (hereunder referred to as "L-Arg-OMe.HCl") was dissolved in the L-Ala-TBP such that the concentration of the former was set at a level of 200 mmol/kg-L-Ala-TBP (the amount of water relative to the total mass of the reaction system: less than 1% by mass) and that the reaction time period was changed from 20 hours to 50 hours. Thus, the intended dipeptide, i.e., L-arginyl alanine (L-Arg-Ala) was synthesized and in this respect, the formation of the intended dipeptide, i.e., L-Arg-Ala was confirmed according to the HPLC analysis.

The foregoing L-Arg-OMe.HCl used above is commercially available, and it was purchased from BACHEM Company.

The yield of L-Arg-Ala obtained by the foregoing reaction carried out at 60° C. for 50 hours was found to be 80.0% by mole relative to the amount of L-Arg-OMe.HCl added to the reaction system at the initiation of the reaction.

Example 12

Synthesis of Dipeptide, i.e., L-Ala-his

The same procedures used in Example 9 were repeated except that L-His-TBP, which was purchased from KATAYAMA Drug-Manufacturing Laboratory was used in place of the L-Gln-TBP employed in Example 9 and that L-alanine methyl ester hydrochloride (hereunder referred to as "L-Ala-OMe.HCl") was dissolved in the L-His-TBP such that the concentration of the former was set at a level of 200 mmol/kg-L-His-TBP (the amount of water relative to the total mass of the reaction system: less than 1% by mass) to synthesize the intended dipeptide, i.e., L-alanyl histidine (L-Ala-His) and to confirm the dipeptide, i.e., L-Ala-His, according to the HPLC technique.

The L-Ala-OMe.HCl used above is a commercially available, and it was purchased from Tokyo Chemical Industry Co. Ltd.

The yield of L-Ala-His obtained by the foregoing reaction carried out at 60° C. for 20 hours was found to be 3.3% by mole relative to the amount of L-Ala-OMe.HCl added to the reaction system at the initiation of the reaction.

Example 13

Synthesis of Dipeptide, i.e., L-Arg-Gly

The same procedures used in Example 8 were repeated except that L-glycine (L-Gly) was substituted for the L-Ala used in Example 8 to subject the components to a dehydration condensation reaction and to obtain glycine-tetrabutyl phosphonium (hereunder referred to as "Gly-TBP") as a colorless and transparent liquid.

Subsequently, the same procedures used in Example 8 were also repeated except that L-arginine methyl ester hydrochloride (hereunder referred to as "L-Arg-OMe.HCl") was dissolved in the Gly-TBP obtained such that the concentration of the former was set at a level of 200 mmol/kg-Gly-TBP (the amount of water relative to the total mass of the reaction system: 16% by mass) and that the reaction time period was changed from 23 hours to 24 hours to thereby synthesize the desired dipeptide, i.e., L-arginyl glycine (L-Arg-Gly) and to confirm the dipeptide, i.e., L-Arg-Gly.

The amino acids, i.e., L-Gly and L-Arg-OMe.HCl used above are commercially available, and they were purchased from Sigma Company and BACHEM Company, respectively.

The yield of L-Arg-Gly obtained by the foregoing reaction carried out at 60° C. for 24 hours was found to be 94.0% by mole relative to the amount of L-Arg-OMe.HCl added to the reaction system at the initiation of the reaction.

Example 14

Synthesis of Dipeptide, i.e., L-Gly-Cys

The same procedures used in Example 8 were repeated except that L-cystine-tetrabutyl phosphonium (hereunder referred to as "L-Cys-TBP"), which was purchased from KATAYAMA Drug-Manufacturing Laboratory was used in place of the Gly-TBP employed in Example 8, that glycine methyl ester hydrochloride (hereunder referred to as "Gly-OMe.HCl") was dissolved in the L-Cys-TBP such that the concentration of the former was set at a level of 200 mmol/kg-L-Cys-TBP (the amount of water relative to the total mass of the reaction system: less than 1% by mass) and that the reaction time period was changed from 23 hours to 2 hours. Thus, the title dipeptide, i.e., glycyl cysteine (L-Gly-Cys) was prepared and in this respect, the formation thereof was confirmed by the HPLC analysis.

The Gly-OMe.HCl used above is commercially available, and it was purchased from WATANABE Chemical Industry Co., Ltd.

The yield of the intended dipeptide, i.e. Gly-Cys obtained by the foregoing reaction carried out at 60° C. for 2 hours was found to be 90.0% by mole relative to the amount of Gly-OMe.HCl added to the reaction system at the initiation of the reaction.

Example 15

Synthesis of Dipeptide, i.e., L-Arg-Ala

The same procedures used in Example 8 were repeated except that L-alanine-1-ethyl-3-methyl imidazolium (hereunder referred to as "L-Ala-EMIM"), which was purchased from KATAYAMA Drug-Manufacturing Laboratory was used in place of the Gly-TBP employed in Example 8, that L-arginine methyl ester hydrochloride (hereunder referred to as "L-Arg-OMe.HCl") was dissolved in the L-Ala-EMIM such that the concentration of the former was set at a level of 200 mmol/kg-L-Ala-EMIM (the amount of water relative to the total mass of the reaction system: 0.12% by mass) and that the reaction time period was changed from 23 hours to 95 hours. Thus, the title dipeptide, i.e., L-arginyl alanine (L-Arg-Ala) was prepared and in this respect, the formation thereof was confirmed by the HPLC analysis.

The L-Arg-OMe.HCl used above is commercially available, and it was purchased from BACHEM Company.

The yield of the intended dipeptide, i.e., L-Arg-Ala obtained by the foregoing reaction carried out at 60° C. for 95 hours was found to be 82.9% by mole relative to the amount of L-Arg-OMe.HCl added to the reaction system at the initiation of the reaction.

Example 16

Synthesis of Dipeptide, i.e., L-Arg-Gly

The same procedures used in Example 8 were repeated except that glycine-1-ethyl-3-methyl imidazolium (hereunder referred to as "Gly-EMIM"), which was purchased from KATAYAMA Drug-Manufacturing Laboratory was used in place of the Gly-TBP employed in Example 8, that L-arginine methyl ester hydrochloride (hereunder referred to as "L-Arg-OMe.HCl") was dissolved in the Gly-EMIM such that the concentration of the former was set at a level of 200 mmol/kg-Gly-EMIM (the amount of water relative to the total mass of the reaction system: 0.50% by mass) and that the reaction time period was changed from 23 hours to 95 hours. Thus, the title dipeptide, i.e., L-arginyl glycine (L-Arg-Gly) was prepared and in this respect, the formation thereof was confirmed by the HPLC analysis.

The L-Arg-OMe.HCl used above is commercially available, and it was purchased from BACHEM Company.

The yield of the intended dipeptide, i.e., L-Arg-Gly obtained by the foregoing reaction carried out at 60° C. for 95 hours was found to be 102.5% by mole relative to the amount of L-Arg-OMe.HCl added to the reaction system at the initiation of the reaction.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for producing a peptide, which comprises:
   (a) mixing (A) a first amino acid or peptide, which is converted into its ionic liquid form through the formation of an ionic bond, with (B) an ester of second amino acid or peptide, to obtain a reaction system; and
   (b) reacting said (A) first amino acid or peptide with said (B) an ester of second amino acid or peptide, in the absence of any peptide hydrolase and in the absence of any condensation agent, in the presence of water in an amount of not more than 20% by mass relative to the total mass of the reaction system to form a peptide bond between said first amino acid or peptide and said second amino acid or peptide.

2. The method according to claim 1, wherein (A) said first ammo acid or peptide, which is converted into its ionic liquid form, is reacted with (B) said ester of second amino acid or peptide, under a condition that the water present in the reaction system is dissolved or dispersed in (A) said first amino acid or peptide, which is converted into its ionic liquid form, and at least part of (B) said ester of second amino acid or peptide is dissolved in (A) the first amino acid or peptide, which is converted into its ionic liquid form.

3. The method according to claim 1, wherein the molar ratio of said first amino acid or peptide to said second amino acid or peptide is within the range of from 20:1 to 1:1.

4. The method according to claim 2, wherein the molar ratio of said first amino acid or peptide to said second amino acid or peptide is within the range of from 20:1 to 1:1.

5. The method according to claim 1, wherein said first ammo acid or peptide has a secondary amino group within the molecule.

6. The method according to claim 2, wherein said first amino acid or peptide has a secondary amino group within the molecule.

7. The method according to claim 3, wherein said first amino acid or peptide has a secondary amino group within the molecule.

8. The method according claim 1, wherein said second amino acid or peptide is free of any protective group at its amino group.

9. The method according to claim 2, wherein said second amino acid or peptide is free of any protective group at its amino group.

10. The method according claim 3, wherein said second amino acid or peptide is free of any protective group at its amino group.

11. The method according to claim 1, wherein said second amino acid or peptide is protected at its amino group.

12. The method according to claim 2, wherein said second amino acid or peptide is protected at its amino group.

13. The method according to claim 3, wherein said second amino acid or peptide is protected at its amino group.

14. The method according to claim 1, wherein said second amino acid or peptide is a mixture of two or more of second amino acids or peptides.

15. The method according to claim 2, wherein said second amino acid or peptide is a mixture of two or more of second amino acids or peptides.

16. The method according to claim 3, wherein said second ammo acid or peptide is a mixture of two or more of second amino acids or peptides.

17. The method according to claim 1, wherein the peptide bond is formed between the amino group of the first amino acid or peptide and the carboxyl group of the second amino acid or peptide.

18. The method according to claim 1, wherein said first amino acid or peptide is converted into its ionic liquid form through the formation of an ionic bond of at least one amino acid or peptide and at least one cation selected from the group consisting of an alkyl phosphonium ion, an alkyl imidazolium ion, an alkyl ammonium ion, an alkyl pyridinium ion, an alkyl pyrrolidinium ion, and an alkyl piperidinium ion.

19. The method according to claim 1, wherein said peptide bond is formed at a temperature ranging from 0 to 100° C.

20. The method according to claim 1, wherein the water present in the reaction system is in an amount of not more than 10% by mass relative to the total mass of the reaction system.

21. A method for producing a peptide, which comprises:
   (a) mixing (A) a first amino acid or peptide, which is converted into its ionic liquid form through the formation of an ionic bond, with (B) an ester of second amino acid or peptide, to obtain a reaction system; and
   (b) reacting said (A) first amino acid or peptide with said (B) an ester of second amino acid or peptide, in a reaction system which is substantially free of any peptide hydrolase and substantially free of any condensation agent, in the presence of water in an amount of not more than 20% by mass relative to the total mass of the reaction system to form a peptide bond between said first amino acid or peptide and said second amino acid or peptide.

* * * * *